United States Patent [19]
Vaitekunas et al.

[11] Patent Number: 5,275,166
[45] Date of Patent: Jan. 4, 1994

[54] METHOD AND APPARATUS FOR PERFORMING ULTRASONIC ASSISTED SURGICAL PROCEDURES

[75] Inventors: Jeffrey J. Vaitekunas, West Chester; Thomas F. Charlebois, Cleveland, both of Ohio

[73] Assignee: Ethicon, Inc., Cincinnati, Ohio

[21] Appl. No.: 977,087

[22] Filed: Nov. 16, 1992

[51] Int. Cl.$^5$ ............................................. A61B 8/12
[52] U.S. Cl. ........................ 128/660.03; 128/662.03; 128/662.05
[58] Field of Search ............... 128/660.03, 661.08, 128/662.03, 662.04, 662.05, 662.06, 663.01

[56] References Cited

U.S. PATENT DOCUMENTS

| | | | |
|---|---|---|---|
| 4,567,896 | 2/1986 | Barnea et al. | 128/662.05 |
| 4,582,067 | 4/1986 | Silverstein et al. | 128/662.05 |
| 4,770,185 | 9/1988 | Silverstein et al. | 128/661.08 |
| 4,867,169 | 9/1989 | Machida et al. | 128/662.03 |
| 4,887,606 | 12/1989 | Yock et al. | 128/662.05 |
| 5,080,103 | 1/1992 | Olivier | 128/662.05 |
| 5,080,104 | 1/1992 | Marks et al. | 128/662.05 |
| 5,085,220 | 2/1992 | Nudell et al. | 128/661.09 |
| 5,115,814 | 5/1992 | Griffith et al. | 128/662.06 |

*Primary Examiner*—William E. Kamm
*Assistant Examiner*—George Manuel
*Attorney, Agent, or Firm*—Killworth, Gottman, Hagan & Schaeff

[57] ABSTRACT

Ultrasonic sensing systems are incorporated into surgical instruments to monitor operational fields defined by distal ends of the instruments. The instruments include proximal ends for their activation typically including one or a pair of handles which a surgeon grasps and operates, for example by squeezing the handles together or by pivotally moving a trigger portion of the handle relative to a fixed portion of the handle. Circuitry for performing ultrasonic sensing preferably is enclosed in housings defined within the handles of the proximal ends of the instruments. Wiring, preferably running through the instruments, connects the circuitry to transducers formed in or mounted on the distal ends of the surgical instruments. The transducers direct ultrasonic energy to the operational fields defined by the distal ends of the instruments and receive ultrasonic energy reflected from the operational fields. The direction for transmission and receipt of ultrasonic energy is determined by acoustic lenses, angularly oriented transducer mounts or a combination of the two. Signals representative of the tissue or contents of the operational fields of surgical instruments drive audible signal generators or preferably tactile transducers to inform the surgeon of the contents. Tactile transducers are mounted for access by the surgeon, preferably on the handles of the surgical instruments.

23 Claims, 8 Drawing Sheets

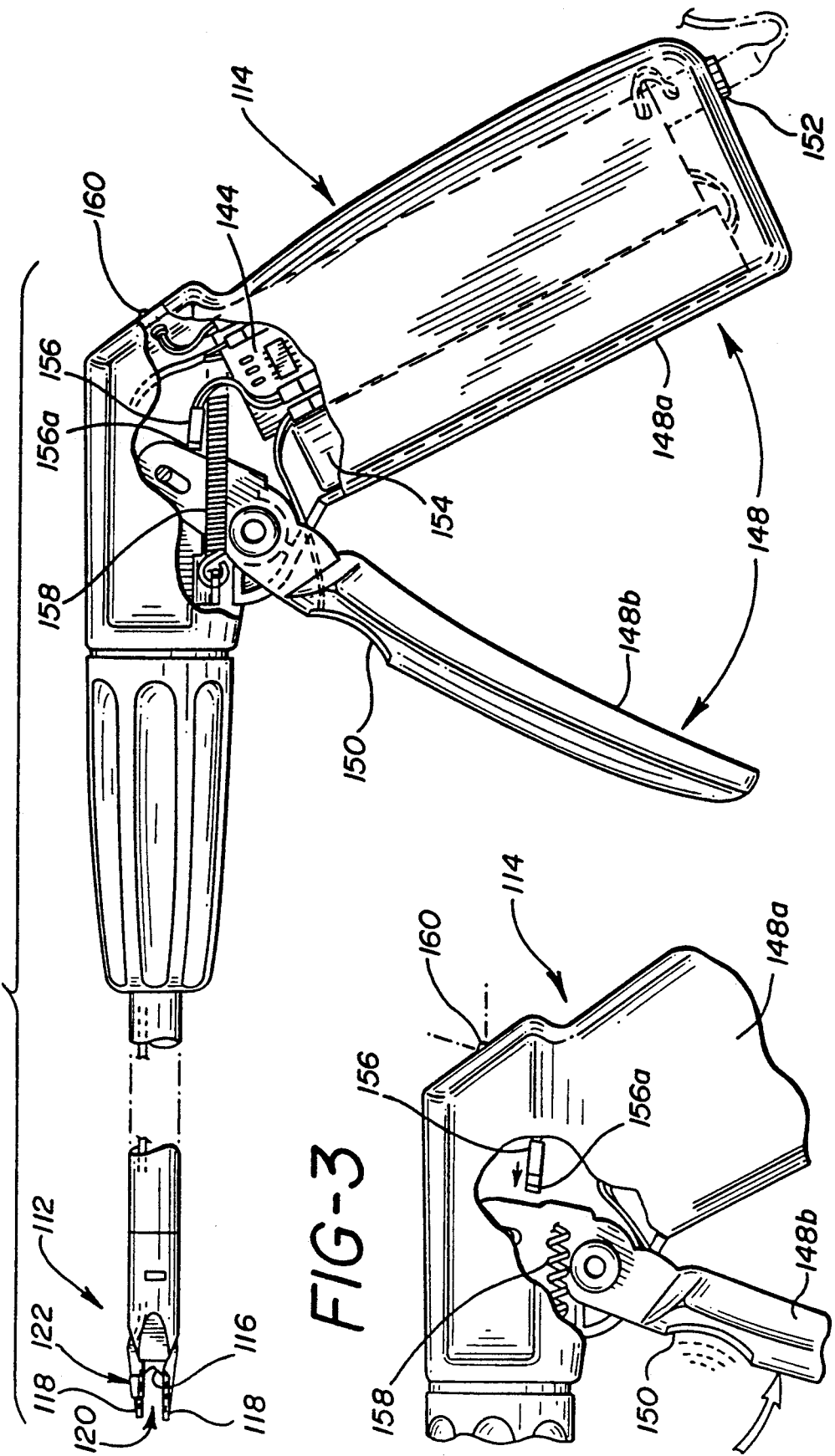

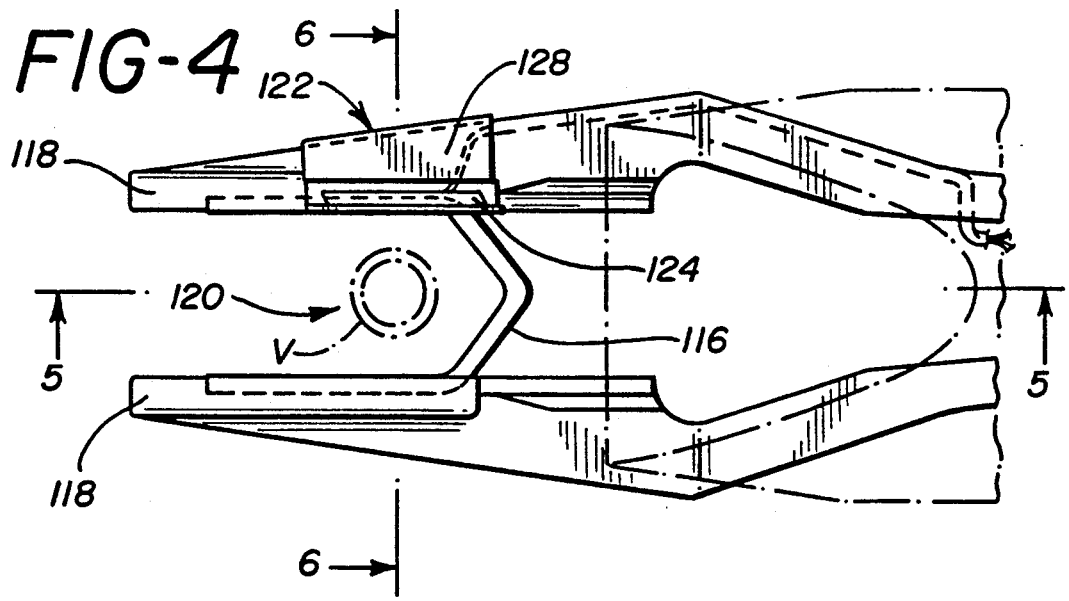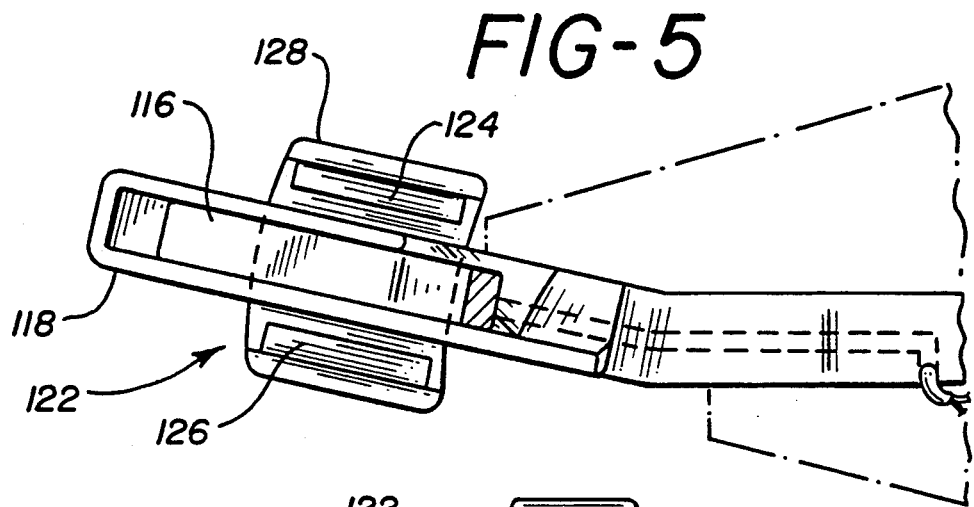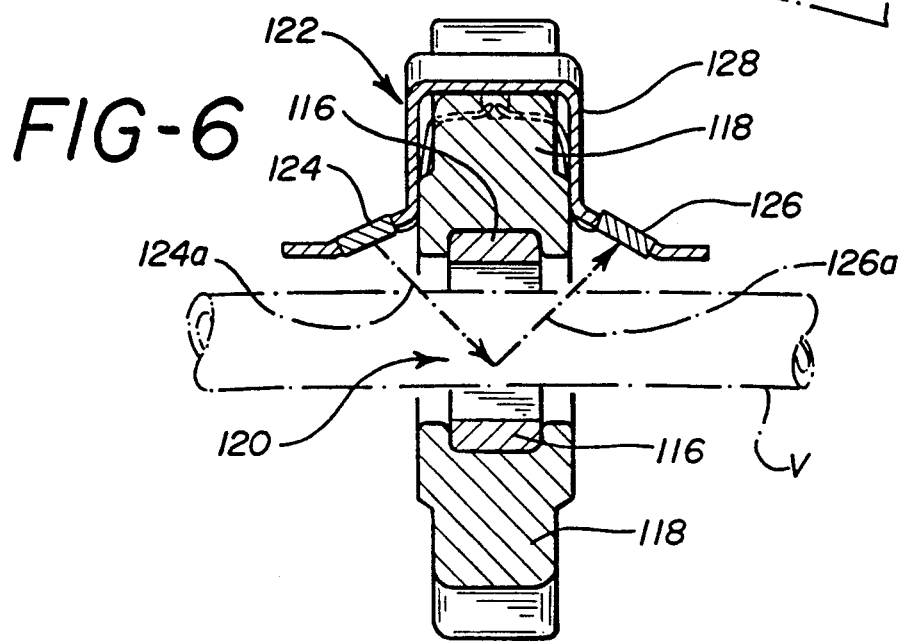

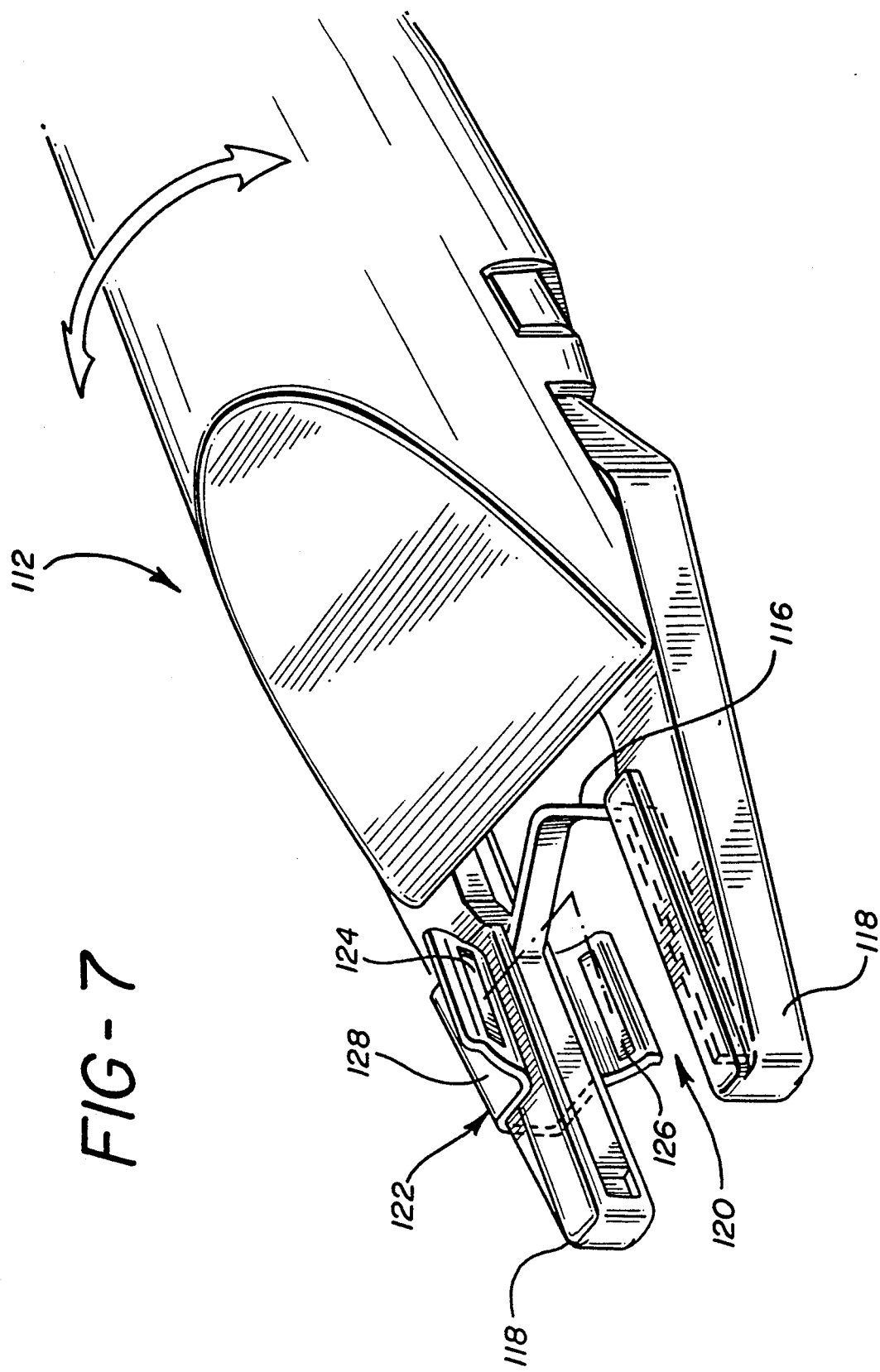

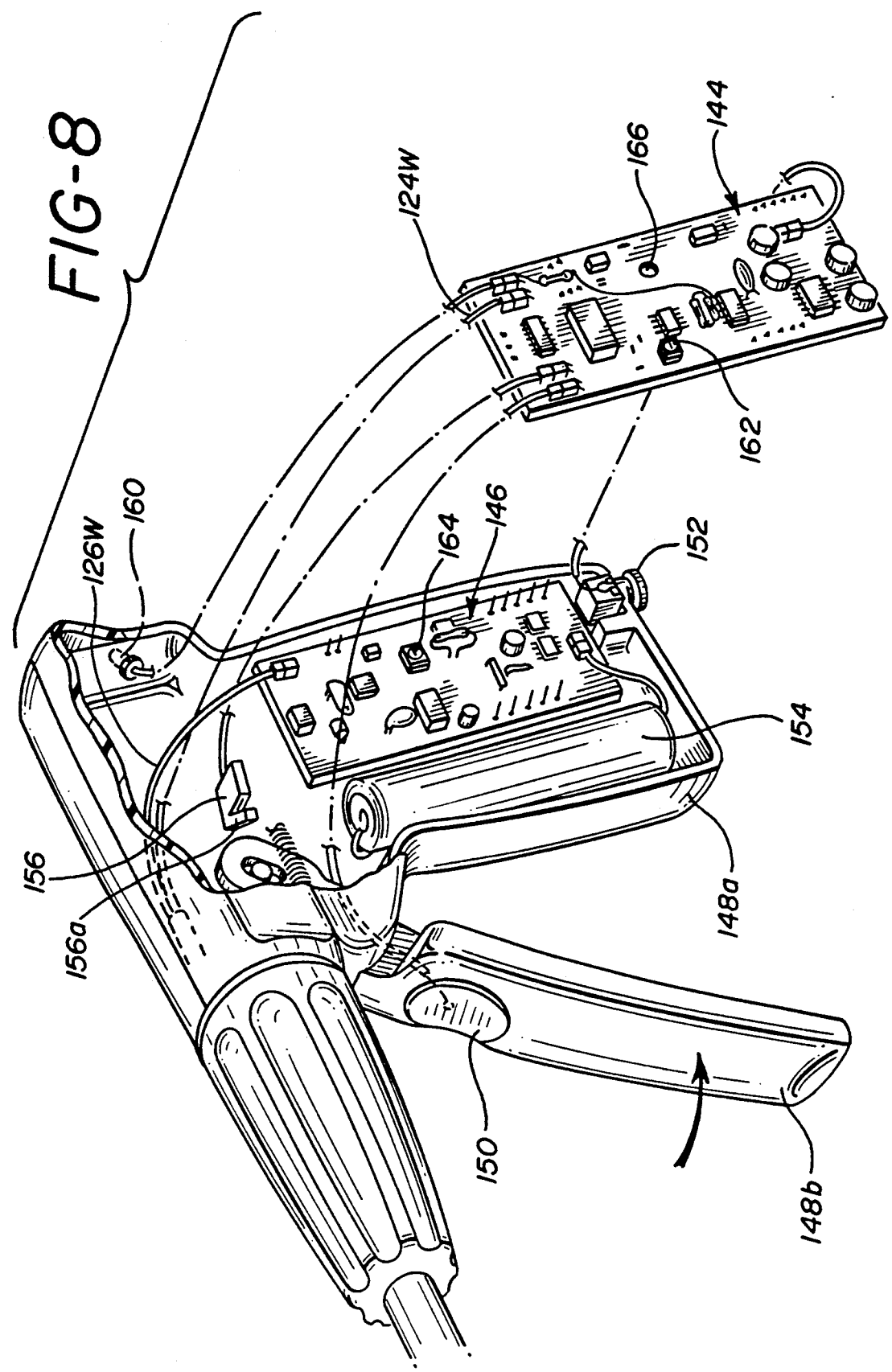

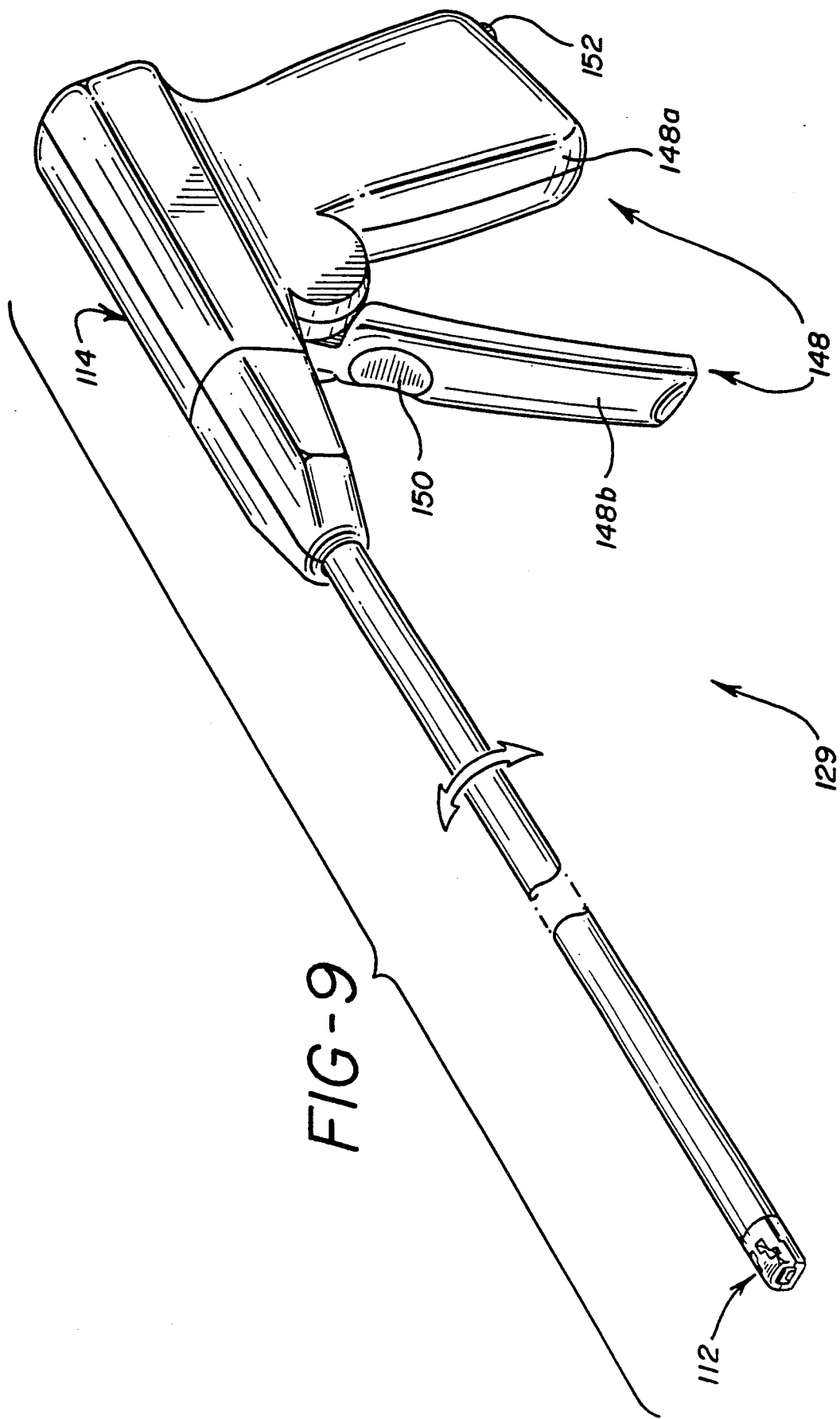

METHOD AND APPARATUS FOR PERFORMING ULTRASONIC ASSISTED SURGICAL PROCEDURES

BACKGROUND OF THE INVENTION

The present invention relates in general to the performance of a variety of surgical steps or procedures during surgical operations and, more particularly, to methods and apparatus for utilizing ultrasonic sensing as an integral part of such surgical procedures to expedite and facilitate their performance and to extend a surgeon's sense of "feel". While the methods and apparatus of the present invention are generally applicable to the performance of these surgical procedures during any operation, they are particularly applicable to their performance during endoscopic surgery and, accordingly, will be described herein with reference to this application.

The scope of surgical operations which can be performed using endoscopic surgery is constantly being expanded. Endoscopic surgery is often preferred due to its limited invasive nature and the corresponding reduced recovery time. For example, in an endoscopic procedure performed within the abdomen, rather than making a relatively large abdominal wall opening for surgical access, small cannulas are inserted through the abdominal wall with endoscopic instruments being inserted through the cannulas and manipulated by a surgeon to perform the endoscopic surgery.

Two operations which commonly can be performed to advantage using endoscopic surgical techniques are gall bladder surgery and surgical repair of an abdominal hernia. In both instances, one cannula permits introduction of a combination illuminating and viewing instrument and a second cannula permits introduction of a number of different endoscopic surgical instruments which are used for performing surgical steps or procedures required to complete the surgical operation prior to removing the cannulas and closing the relatively small openings required for their insertion.

A problem in using certain surgical instruments that is particularly apparent during endoscopic surgery is the lack of the surgeon's sense of feel. In non-endoscopic surgery, a surgeon can normally easily verify the identification of structures within a conventional surgical opening. In particular in the two noted operations, the surgeon normally uses the sense of feel to verify the nature of visually identified vessels.

In a gall bladder operation, for example, the bile duct must be distinguished from a blood vessel which passes close to the duct. The locations of blood vessels must be determined in the repair of an abdominal hernia using endoscopic surgery since such repair is performed by stapling a section of polymeric mesh material to the inside of the abdominal wall. The material securing staples must be placed to ensure that a blood vessel is not stapled during the repair.

The identification of blood vessels during endoscopic surgical operations has been addressed in the prior art. For example, in U.S. Pat. No. 4,770,185 issued to Silverstein et al, an ultrasonic probe is disclosed wherein pulsed ultrasonic energy is used in a catheter to identify both venous and arterial blood flow. A resulting Doppler signal is used to drive a loudspeaker such that the sense of hearing is used in place of the surgeon's sense of feel.

In one of the embodiments disclosed in Silverstein et al, vessels are identified prior to use of a separate instrument, such as a papillotome catheter. For this embodiment, the ultrasonic probe must first be inserted through a cannula, utilized for identification of vessels, and withdrawn from the cannula to permit insertion of the papillotome catheter.

Silverstein et al's ultrasonic probe is also disclosed as being incorporated into the end of a papillotome catheter, such that blood vessels can be sensed as the catheter is advanced toward an operating position, and into the end of a catheter through which a needle may be deployed. The scanning direction of the ultrasonic probes is disclosed as being selectable to be highly directional, sectorially directed or omnidirectional. However, in the disclosed combination ultrasonic probe/catheter embodiments, while the ultrasonic scanning and surgical procedures can be performed without removal and replacement of catheters, the scanning is not directed to the operational region of the associated catheters.

Accordingly, there is a need for improved ultrasonically assisted surgical procedures which can be utilized in a growing number of surgical instruments, including and with particular benefit for endoscopic surgical instruments, wherein the ultrasonic monitoring is performed within an operational field of the surgical instrument. Such improved ultrasonically assisted surgical procedures would permit monitoring within the operational field prior to, during and after a surgical procedure to help ensure successful performance and completion of the procedure. While the results of the ultrasonic sensing can be audibly produced, preferably the improved ultrasonically assisted surgical procedures would extend and restore the surgeon's sense of feel for performance of surgical procedures.

SUMMARY OF THE INVENTION

This need is met by the methods and apparatus of the present invention wherein an ultrasonic sensing system is incorporated into a surgical instrument such that it is used to monitor an operational field defined by a distal end of the surgical instrument. Surgical instruments operable in accordance with the present invention also include a proximal end for activating the surgical instrument. The proximal ends of the surgical instruments typically include one or a pair of handles which the surgeon grasps and operates, for example by squeezing the handles together or by pivotally moving a trigger portion of the handle relative to a fixed portion of the handle.

To merge ultrasonic sensing systems and surgical instruments efficiently, circuitry for performing ultrasonic sensing is preferably enclosed in housings defined within the handles of the proximal ends of the instruments. Wiring, preferably running through the instruments, connects the circuitry to transducers formed in or mounted on the distal ends of the surgical instruments. The transducers direct ultrasonic energy to the operational fields defined by the distal ends of the instruments and receive ultrasonic energy reflected from the operational fields. The direction for transmission and receipt of ultrasonic energy is determined by ultrasonic energy directing means which can comprise acoustic lenses, angularly oriented transducer mounts or a combination of the two.

Signals representative of the tissue or contents of the operational field of a surgical instrument and generated by the ultrasonic sensing system are used to drive alerting means. While the alerting means can take a variety of forms, such as an audible signal generator, preferably the alerting means comprises tactile transducer means for tactilely alerting the surgeon. The tactile transducer is mounted for access by the surgeon and preferably on the handle of the surgical instrument. In this way, the present invention extends and restores a surgeon's sense of feel for performance of surgical procedures, particularly endoscopic surgical procedures. The sensitivity of the ultrasonic sensing system can be adjusted to prevent activation of the alerting means for background signal levels. The level of the alerting signal, whether audible or tactile, can also be adjusted.

In accordance with one aspect of the present invention, a surgical instrument having a distal end for performing a surgical step and a proximal end for activating performance of the surgical step is combined with an ultrasonic sensing system. The combination comprises ultrasonic transducer means associated with the distal end of the surgical instrument for transmitting ultrasonic energy to an operational field defined by the distal end of the surgical instrument, for receiving ultrasonic energy reflected from the operational field, and for generating signals representative of ultrasonic energy received by the ultrasonic transducer means. Circuit means is coupled to the ultrasonic transducer means for activating the transducer means to transmit ultrasonic energy and to receive and analyze the signals received from the ultrasonic transducer means. Alerting means is coupled to the circuit means for informing a surgeon using the surgical instrument of the contents of the operational field.

Preferably, the alerting means comprises tactile transducer means coupled to the proximal end of the surgical instrument for tactilely alerting the user to thereby extend and restore the using surgeon's sense of feel. Alternately, the alerting means may comprise an audible signal generator such as a speaker or earphone.

The ultrasonic transducer means comprises directing means for directing the transmission and reception of the ultrasonic energy upon the operational field. For example, when the ultrasonic transducer means comprises an ultrasonic transmitter and an ultrasonic receiver, the directing means may comprise transmitter acoustic lens means for focusing transmitted ultrasonic energy toward the operational field and receiver acoustic lens means for focusing ultrasonic energy from the operational field upon the ultrasonic receiver. Alternately or in combination with acoustic lens means, the directing means may comprise mounting means for supporting the ultrasonic transmitter to direct the ultrasonic transmitter at the operational field and for supporting the ultrasonic receiver to direct the ultrasonic receiver at the operational field.

In many of the possible embodiments of the present invention, the distal end of the surgical instrument comprises at least two members which are movable relative to one another for performing the surgical step within the operational field. For these embodiments, the directing means may comprise mounting means secured to one of the at least two members. The mounting means angularly support the ultrasonic transmitter relative to the one of the at least two members to aim the ultrasonic transmitter at the operational field and similarly angularly support the ultrasonic receiver relative to the one of the at least two members to aim the ultrasonic receiver at the operational field. For example, the mounting means may comprise a bracket angularly supporting the ultrasonic transmitter on a first side of the one of the at least two members to aim the ultrasonic transmitter at the operational field and angularly supporting the ultrasonic receiver on a second side of the one of the at least two members opposite to the first side to aim the ultrasonic receiver at the operational field.

In one of the illustrated embodiments, the surgical instrument comprises a surgical fastener applier with the distal end comprising a fastener ejection end and the proximal end comprising a handle grasped and operated by the user. For this embodiment, the circuit means is housed within the handle and interconnected to the transducer means by wires extending from the handle to the fastener ejection end. In the illustrated embodiments, the ultrasonic means operates at a frequency of approximately 20 megahertz. To extend the shelf life and conserve power during usage of battery operated combinations in accordance with the present invention, power control means are coupled to the circuit means and the surgical instrument for connecting power to the circuit means only while the surgical instrument is at least partially activated.

In accordance with another aspect of the present invention, an ultrasonic sensing system is incorporated into a surgical instrument having a distal end for performing a surgical procedure and a proximal end for activating performance of the surgical procedure. The resulting surgical instrument comprises ultrasonic transducer means associated with its distal end for transmitting ultrasonic energy to an operational field defined by the distal end of the surgical instrument, for receiving ultrasonic energy reflected from the operational field, and for generating signals representative of ultrasonic energy received by the ultrasonic transducer means from the operational field. Circuit means is coupled to the ultrasonic transducer means for driving the transducer means to transmit the ultrasonic energy and for receiving and analyzing the signals from the ultrasonic transducer means. Alerting means are coupled to the circuit means for informing a user of the surgical instrument of the contents of the operational field.

The circuit means comprises comparator means for comparing a doppler signal derived from the signals to a threshold signal for analyzing the signals and preferably further comprises threshold adjustment means for setting the threshold signal.

In accordance with yet another aspect of the present invention, a method of operating a surgical instrument having a distal end for performing a surgical procedure within an operational field defined by the distal end and a proximal end for activating performance of the surgical procedure within the operational field comprises the steps of: transmitting ultrasonic energy to the operational field of the surgical instrument; receiving ultrasonic energy reflected from the operational field of the surgical instrument; generating doppler signals representative of the contents of the operational field in response to reflected ultrasonic energy received from the operational field; analyzing the doppler signals to determine the nature of the contents of the operational field of the surgical instrument; informing the user of the surgical instrument of the contents of the operational field; and, operating the surgical instrument to perform the surgical procedure in response to information confirming that the contents of the operational field are appropriate for the surgical procedure.

The step of informing the user of the surgical instrument of the contents of the operational field preferably comprises the step of activating tactile transducer means accessible to the user for tactilely informing the user. To extend the shelf life and conserve power during usage of battery operated surgical instruments in accordance with the present invention, the method may further comprise the step of enabling the performance of the foregoing method steps only while the surgical instrument is at least partially operated.

The step of analyzing the doppler signals may comprise comparing the doppler signals to a threshold and the step of informing the user of the surgical instrument of the contents of the operational field may comprise activating an alerting device while the signals exceed the threshold which may be adjustable. The step of informing the user of the contents of the operational field preferably comprises activating tactile transducer means accessible to the user. Alternately, audible transducer means may be activated.

It is thus an object of the present invention to provide improved methods and apparatus for ultrasonically assisted surgical procedures which can be utilized in a growing number of surgical instruments, particularly endoscopic surgical instruments; to provide improved methods and apparatus for ultrasonically assisted surgical procedures wherein an ultrasonic sensing system is incorporated into a surgical instrument such that it is used to monitor an operational field defined by a distal end of the surgical instrument; and, to provide improved methods and apparatus for ultrasonically assisted surgical procedures wherein a surgeon's sense of feel is extended and restored when using a surgical instrument by means of the results of ultrasonic sensing being tactilely reported to the surgeon.

Other objects and advantages of the invention will be apparent from the following description, the accompanying drawings and the appended claims.

BRIEF DESCRIPTION OF THE DRAWINGS

FIG. 2 is a side elevational view of the endoscopic ligating clip applier of FIG. 1 which has been partially broken away to reveal structural details of the incorporation of an ultrasonic sensing system into the clip applier;

FIG. 3 is a fragmentary side view of the clip applier of FIG. 2 showing actuation of the ultrasonic sensing system;

FIGS. 4-7 show incorporation of an ultrasonic transmitter and an ultrasonic receiver into the distal end of the endoscopic ligating clip applier of FIGS. 1-3;

FIG. 8 is a fragmentary, partially exploded perspective view of piggy-back mounting of two printed circuit boards in a handle of the endoscopic clip applier of FIGS. 1-3;

FIG. 9 is a perspective view of another embodiment of the present invention wherein an endoscopic stapler incorporates an ultrasonic sensing system;

DETAILED DESCRIPTION OF THE INVENTION

Figure 1:
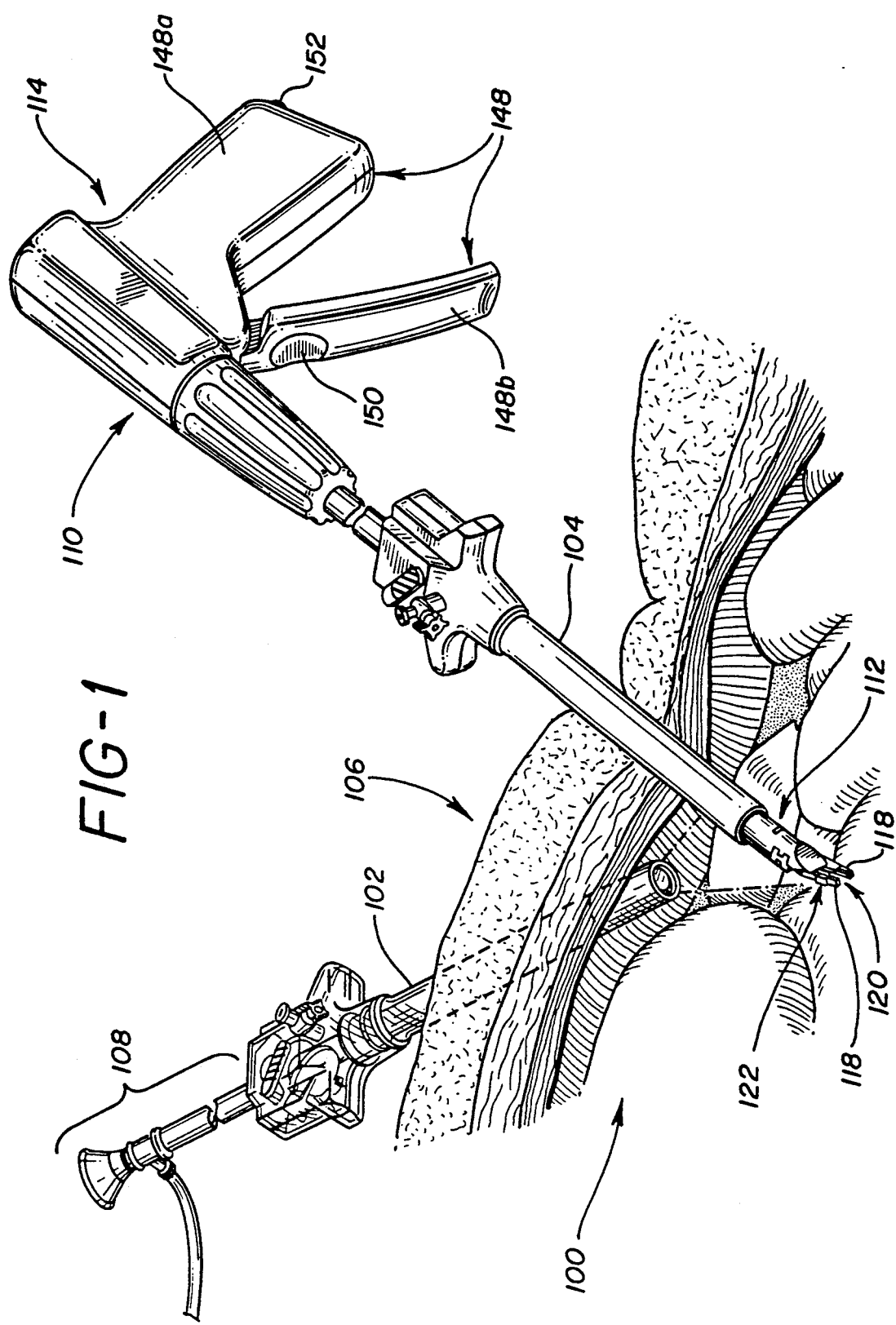
FIG. 1 is a partially sectioned perspective view of an endoscopic abdominal surgical operation being performed with an endoscopic ligating clip applier constructed and operable in accordance with the present invention.

The methods and apparatus of the present invention will now be described with reference to the drawing figures. While the invention is generally applicable to the performance of surgical procedures during any operation, it is particularly applicable to the performance of surgical procedures during endoscopic operations and, accordingly, will be described herein with primary emphasis on this application.

The environment for performing an endoscopic surgical procedure within an abdomen 100 is illustrated in FIG. 1. Rather than the large abdominal wall opening required for surgical access in non-endoscopic procedures, first and second cannulas 102, 104 have been inserted through the various layers of an abdominal wall 106. Endoscopic instruments are inserted through the cannulas 102, 104 and manipulated by a surgeon to perform the endoscopic surgery.

As shown in FIG. 1, the first cannula 102 is used for insertion of a combination illuminating and viewing instrument 108. The second cannula 104 is used for insertion of endoscopic surgical instruments, represented by an endoscopic ligating clip applier 110 in FIG. 1, which are used for performing surgical steps or procedures required to complete the surgical operation. Once the surgical operation is completed, the cannulas 102, 104 are removed and the relatively small openings required for their insertion are closed.

The endoscopic ligating clip applier 110 shown in FIG. 1 is constructed and operable in accordance with the invention of the present application. The clip applier 110 has a distal end 112 for performing a step in a surgical operation and a proximal end 114 for activating performance of the surgical step. For the clip applier 110, the surgical step is the application of ligating clips 116, best shown in FIGS. 2 and 4-7, to vessels to be closed. A plurality of ligating clips 116 are contained within clip applier 110.

The clips 116 are retained between two members or jaws 118 at the distal end 112 of the clip applier 110. The clips 116 are passed to the jaws 118 in a generally u-shaped, open form and positioned around a vessel V to be ligated. The jaws 118 are then closed to close and secure one of the clips 116 about the vessel V. The clips 116 are applied within an operational field 120 defined by the distal end 112 of the clip applier 110 and, more particularly, by the opening between the jaws 118.

Since the mechanical structure of the clip applier 110, as well as other surgical instruments which incorporate ultrasonic sensing systems operable in accordance with the present invention, do not form part of the invention, they will be described herein only to the extent necessary to fully understand the invention. The clip applier 110 is commercially available from the assignee of the present application under the trademark LIGACLIP ERCA and is the subject of U.S. patent application Ser. No. 779,420, filed Oct. 17, 1991.

As shown in FIGS. 1 and 2, an ultrasonic sensing system is combined with the clip applier 110 to form an improved surgical instrument. Ultrasonic transducer means 122 are associated with the distal end 112 or fastener ejection end of the clip applier 110. As best shown in FIGS. 4–7, the ultrasonic transducer means 122 comprises an ultrasonic transmitter 124, an ultrasonic receiver 126 and ultrasonic energy directing means for directing the transmission and the reception of ultrasonic energy on the operational field 120.

In the ultrasonic transducer means of FIGS. 1-2 and 4–7, the ultrasonic energy directing means comprises mounting means taking the form of a mounting bracket 128 which is secured to one of the jaws 118. The mounting bracket 128 supports the ultrasonic transmitter 124 and the ultrasonic receiver 126, directing the transmitter 124 and the receiver 126 at the operational field 120. Acoustic lenses may also be utilized with a transmitter and/or a receiver to direct ultrasonic energy to and from the operational field 120 of a surgical instrument, as will be described with reference to alternate embodiments of the present invention.

In any event, ultrasonic energy from the transmitter 124 is directed to the operational field 120 and reflected back from the contents of the operational field 120 to the receiver 126. The path of the ultrasonic energy for this embodiment of the invention is represented by the arrowed paths 124a and 126a in FIG. 6.

FIGS. 9–12 illustrate the combination of an ultrasonic sensing system and another endoscopic surgical instrument, in this case an endoscopic stapler 129, to form a surgical instrument operable in accordance with the invention of the present application. The stapler 129 is commercially available from the assignee of the present application under the trademarks ENDOSTAPLER ES and ENDOSTAPLER AES. In view of the apparent similarity in appearances of the clip applier 110 and the stapler 129, corresponding elements of the two instruments will be identified by the same numerals. The structure of the stapler will only be described herein as necessary for an understanding of the present invention.

Figure 10:
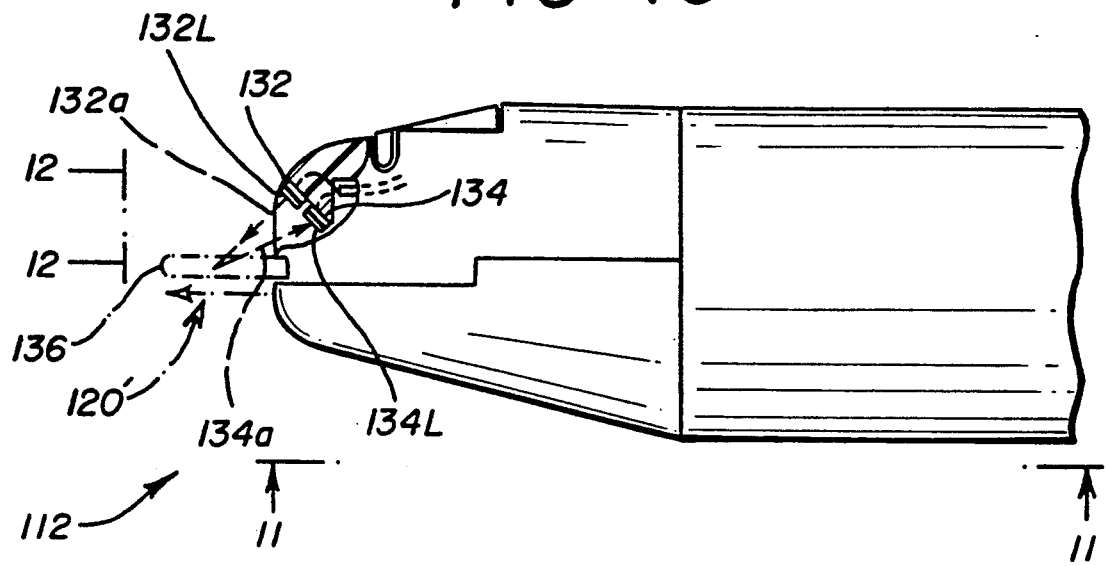
FIG. 10 is a side elevational view of the distal end of the endoscopic stapler of FIG. 9 which has been partially broken away to reveal structural details of the incorporation of ultrasonic transducers therein.
Figure 11:
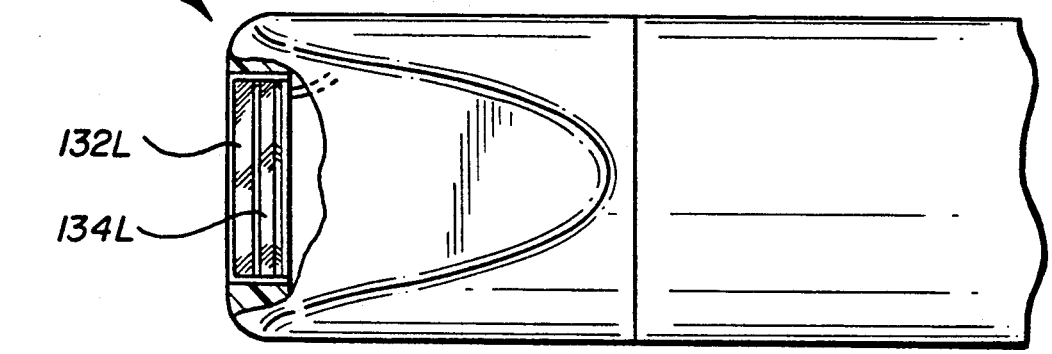
FIG. 11 is a bottom plan view of FIG. 10, taken along the view line 11—11, which has been partially broken away to reveal structural details of the incorporation of the ultrasonic transducers.
Figure 12:
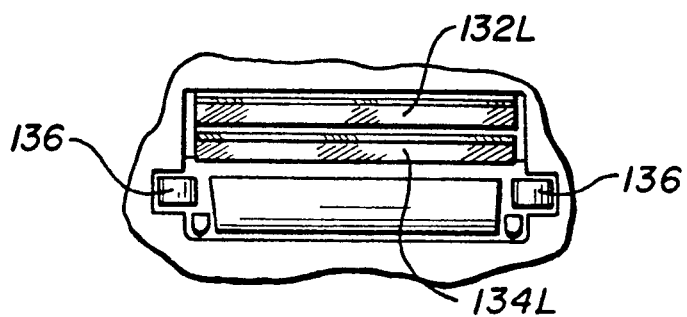
FIG. 12 is a partial front elevational view of FIG. 10 taken along the view line 12—12.

FIG. 10 is a side elevational view of the distal end 112 of the endoscopic stapler of FIG. 9 which has been partially broken away to reveal structural details of the incorporation of ultrasonic transducer means therein. In the endoscopic stapler 129, the ultrasonic transducer means takes the form of an ultrasonic transmitter 132 and an ultrasonic receiver 134.

In this embodiment, the ultrasonic energy directing means includes a transmitter acoustic lens 132L and a receiver acoustic lens 134L. The acoustic lenses 132L and 134L can be made from a number of materials well known in the art to focus the ultrasonic energy as described and shown. Accordingly, the acoustic lenses 132L and 134L will not be further described herein.

The distal end 112 is the fastener or staple ejection end of the stapler with staples 136 being ejected into the operational field 120' of the stapler. In accordance with the present invention, the contents of the operational field 120' is sensed by ultrasonic energy and reported to the surgeon using the stapler 129. The path of the ultrasonic energy for this embodiment of the invention is represented by the arrowed paths 132a and 134a in FIG. 10.

Figure 13:
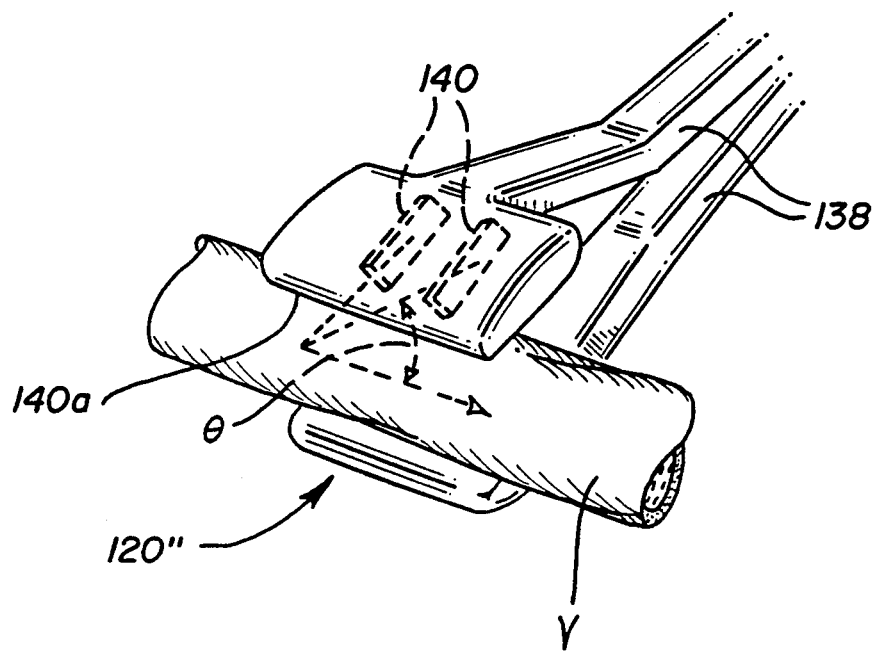
FIG. 13 is a perspective view of a combined blood clamp and ultrasonic sensing system operable in accordance with the present invention.

FIG. 13 illustrates combination of an ultrasonic sensing system into yet another surgical instrument, a blood clamp 138 which is used in conventional surgery as opposed to endoscopic surgery. As shown in FIG. 13, transducer means comprising a pair of ultrasonic transducers 140 are embedded into one side of the blood clamp 138. One of the pair of ultrasonic transducers 140 serves as a transmitter while the other serves as a receiver. The pair of ultrasonic transducers 140 are oriented at an angle of approximately $\theta°$ relative to the clamping surface 140a.

The angular orientation of the pair of ultrasonic transducers 140 preferably is slightly different for each of the transducers 140 such that ultrasonic energy is directed to the operational field 120" occupied by a blood vessel V by the transmitting transducer and reflected back from the operational field 120" to the receiving transducer. Of course, acoustic lenses can be used on one or both of the pair of ultrasonic transducers 140 in place of or in addition to the angular orientation for directing ultrasonic energy associated with the transducers 140 toward or from the operating field 120".

Whatever the form of the ultrasonic transducer means, circuit means are provided for activating the transducer means to transmit ultrasonic energy to the operational field defined by an associated surgical instrument. The circuit means also provides for receiving signals generated by the transducer means in response to received ultrasonic energy which is reflected from the operational field and for analyzing those signals. Since the circuit means is a conventional circuit design as far as transmission and reception of ultrasonic energy and processing of the resulting signals is concerned, it will be described herein only with reference to its assembly and packaging which permits it to be readily combined with surgical instruments. In particular, the assembly and packaging for use in the previously described ligating clip applier 110 will be described. From this description, its application to other surgical instruments will be apparent.

As shown in FIGS. 2, 3 and 8, the circuit means for activating the transducer means of the ligating clip applier 110 is packaged on two printed circuit boards 144, 146. In general, the circuit boards 144, 146 are partitioned such that the upper printed circuit board 144 includes the circuitry for driving the ultrasonic transducer means and the lower printed circuit board 146 includes the circuitry for receiving signals from the transducer means. Accordingly, the upper printed circuit board 144 is connected to the ultrasonic transmitter 124 via wiring 124w and the lower printed circuit board 146 is connected to the ultrasonic receiver via wiring 126w.

In the illustrated embodiment, the circuit means and transducer means are constructed for operation at a frequency of approximately 20 megahertz. While it is apparent that other frequencies can be utilized in accordance with the present invention, the 20 megahertz frequency is used in the illustrated embodiments to better define the focus zone size and depth of penetration of the ultrasonic energy into the tissue.

The circuitry on the boards 144, 146 is of a conventional design. Commercially available components may be surface and otherwise mounted to occupy a limited amount of board space on the boards 144, 146. The boards 144, 146 are also mounted in "piggy-back" fashion, with one board on top of the other to compact the circuitry further and conserve space within the instrument. While external circuitry can be utilized in the present invention, the compact arrangement illustrated is preferred since it is mounted within a first portion 148a of a handle 148 formed at the proximal end 114 of the clip applier 110 to form a compact, self-contained combination instrument. The handle 148 is grasped and operated by a surgeon by pivotally moving a second portion 148b of the handle 148 towards the first portion 148a in a well known manner.

The results of sensing the contents of an operational field, such as the operational fields 120, 120', 120'', are communicated to a surgeon using the clip applier 110 during performance of the surgical procedure, such as for example applying a ligating clip to a vessel. To that end, alerting means are coupled to the circuit means for informing the surgeon of the contents of the operational field. The alerting means may preferably comprise a tactile transducer 150 in the illustrated clip applier 110 of FIGS. 1-3.

The tactile transducer 150 is shown as being positioned within an index finger receiving indentation on the pivotally mounted portion 148b of the handle 148. The transducer 150 may be operated at a frequency of approximately 5 kilohertz. While this position and frequency of operation of the tactile transducer 150 are currently believed to be preferred, it may ultimately be preferred to mount the tactile transducer at other positions on the handle 148 or proximal end 114 of the clip applier 110 which are accessible to the surgeon and to operate the tactile transducer 150 at other frequencies.

Alternate alerting means may comprise a set of headphones, a speaker or the like (not shown) which can be coupled to the circuitry on the boards 144, 146 in the clip applier 110 by means of an electrical jack 152 which is mounted in the base of the first portion 148a of the handle 148. It is also possible to incorporate a sound source directly into the handle 148 which would further simplify the structure of the instrument when audible alerting is used.

In the illustrated embodiment, the circuitry on the boards 144, 146 is operated by power from a battery 154 mounted parallel and adjacent to the boards 144, 146 in the clip applier 110. The battery 154 can be rechargeable in the event the clip applier is to be reusable. For a rechargeable battery, recharging can take place through the jack 152. Alternately, power for the circuit can be provided directly through the jack 152 with elimination of the battery 154.

More likely is the provision of a disposable surgical instrument, such as the clip applier 110. For a disposable instrument, the battery 154 is selected for power levels available from the battery and its shelf life. Currently, for disposable instruments, alkaline, lithium or silver oxide batteries provide sufficiently high power output and have long shelf life.

To be sure that power is not drained from a battery of a battery powered instrument, a power switch 156 is preferably provided to activate the circuitry of the instrument when the pivotally mounted portion 148b of the handle 148 is at least partially operated as shown in FIG. 3. In the illustrated embodiment, the pivotally mounted portion 148b of the handle 148 is biased into an open position spaced from the first portion 148a of the handle 148 by a spring 158.

In the open position of the handle portion 148b shown in FIG. 2, an activating lever 156a of the switch 156 is activated to open normally closed contacts of the switch 156. When the handle portion 148b is moved toward the handle portion 148a of the clip applier 110 by at least a minimum amount, the normally closed contacts of the switch 156 are closed, providing power to the ultrasonic sensing system such that it can sense the contents of the operational field 120 and report the contents to the surgeon.

The ultrasonic sensing system remains active until the first handle portion 148a is allowed to return to its open position under control of the spring 158. To verify activation of the ultrasonic sensing system to a surgeon using the clip applier 110, a light emitting diode 160 or other indicator device located at the proximal end 114 of the clip applier 110 is activated while power is connected to the ultrasonic sensing system.

The circuitry on the printed circuit boards 144, 146 includes two potentiometers 162, 164 with the potentiometer 164 being accessed through an opening 166 in the board 144. One of the potentiometers 162, 164 is used to set the volume of an audible alerting device or the level of signal produced by the tactile transducer while the other one of the potentiometers 162, 164 is used to set a threshold level to which a doppler signal is compared via comparator means included within the circuitry on the circuit boards 144, 146.

If the doppler signal exceeds the set threshold, then the user of the instrument is alerted either tactilely or audibly during that time. The using surgeon is able to detect venous flow, which generates a continuous alerting signal, and arterial flow, which generates a pulsating alerting signal. Further, a vessel such as the bile duct, which does not contain a fluid flowing at a sufficient velocity to generate a doppler signal having an amplitude in excess of the set threshold, may be determined. While it is contemplated that the potentiometers 162, 164 will be set and then sealed during production, it is possible to permit field adjustment by disassembly of the handle 148 or by providing openings (not shown) through the handle 148. Such openings can be sealed, for example, by resilient plugs or the like.

In instruments constructed and operable in accordance with the invention of the present application, a surgeon is able to concentrate on manipulating the instruments into proper positions to perform corresponding surgical procedures, such as clip application or staple insertion. After such positioning, the surgeon can sense ultrasonically thereby extending and returning the surgeon's sense of feeling to determine the contents of the instruments' operational fields prior to performing the procedures.

Even though manipulation of the instruments includes rotation of their distal ends, as shown by the double headed arrows in FIGS. 7 and 9, the ultrasonic sensing system is still properly directed upon the operational fields defined by the instruments facilitating and easing the performance of the surgical procedures. While the wiring interconnecting the circuitry on the circuit boards 144, 146 and the ultrasonic transducers of the instruments can tolerate several rotations of the distal ends of the instruments in one direction, it may be desirable to define rotation stops to limit rotation in either direction to approximately 360°.

While the methods for performing ultrasonically assisted surgical procedures in accordance with the invention of the present application should be apparent from the foregoing description of illustrative embodiments of surgical instruments incorporating ultrasonic sensing systems, an illustrative method of such performance will now be described for sake of clarity. The method is for operating a surgical instrument having a distal end for performing a surgical procedure within an operational field defined by the distal end and a proximal end for activating performance of the surgical procedure within the operational field. Ultrasonic energy is transmitted to the operational field of the surgical instrument and reflected from the contents of the operational field. The ultrasonic energy reflected from the operational field of the surgical instrument is received and doppler signals representative of the contents of the operational field are generated in response to the received ultrasonic energy. The doppler signals are analyzed to determine the nature of the contents of the operational field of the surgical instrument and the user of the surgical instrument is informed of the contents of the operational field. If the contents of the operational field are confirmed as being appropriate for the surgical procedure, the surgical instrument is operated to perform the procedure.

Having thus described the methods and apparatus of the present invention in detail and by reference to preferred embodiments thereof, it will be apparent that modifications and variations are possible without departing from the scope of the invention defined in the appended claims.

What is claimed is:

1. A combination of an ultrasonic sensing system and an endoscopic surgical instrument having a distal end for performing a surgical step and a proximal end for activating performance of said surgical step, said combination comprising:

ultrasonic transducer means associated with said digital end of said endoscopic surgical instrument for transmitting ultrasonic energy to an operational field defined by said distal end of said endoscopic surgical instrument, for receiving ultrasonic energy reflected from said operational field, and for generating signals representative of ultrasonic energy received by said ultrasonic transducer means;

circuit means, coupled to said ultrasonic transducer means and responsive to said signals, for activating said transducer means to transmit said ultrasonic energy and for receiving and analyzing said signals from said ultrasonic transducer means, said circuit means being interconnected to said ultrasonic transducer means by wires extending from said proximal end to said distal end of said endoscopic surgical instrument; and alerting means coupled to said circuit means for informing a user of said endoscopic surgical instrument of the contents of said operational field during performance of said surgical step.

2. A combination as claimed in claim 1 wherein said alerting means comprises an audible signal generator.

3. A combination as claimed in claim 1 wherein said ultrasonic transducer means comprises directing means for fixedly directing the transmission and reception of said ultrasonic energy on said operational field.

4. A combination as claimed in claim 3 wherein said ultrasonic transducer means comprises an ultrasonic transmitter and an ultrasonic receiver, and said directing means comprises a transmitter acoustic lens associated with said transmitter for focusing transmitted ultrasonic energy towards said operational field and a receiver acoustic lens associated with said receiver for focusing ultrasonic energy from said operational field upon said ultrasonic receiver.

5. A combination as claimed in claim 3 wherein said ultrasonic transducer means comprises an ultrasonic transmitter and an ultrasonic receiver, and said directing means comprises mounting means for fixedly supporting said ultrasonic transmitter relative to said endoscopic surgical instrument to direct said ultrasonic transmitter at said operational field and for fixedly supporting said ultrasonic receiver relative to said endoscopic surgical instrument to direct said ultrasonic receiver at said operational field.

6. A combination as claimed in claim 5 wherein said directing means further comprises a transmitter acoustic lens associated with said transmitter for focusing transmitted ultrasonic energy upon said operational field and a receiver lens associated with said receiver for focusing ultrasonic energy from said operational field upon said ultrasonic receiver.

7. A combination as claimed in claim 3 wherein said ultrasonic transducer means comprises an ultrasonic transmitter and an ultrasonic receiver, said distal end of said endoscopic surgical instrument comprises at least two members which are movable relative to one another for performing said surgical step within said operational field, and said directing means comprises mounting means fixedly secured to one of said at least two members for angularly supporting said ultrasonic transmitter relative to said one of said at least two members to aim said ultrasonic transmitter at said operational field and for angularly supporting said ultrasonic receiver relative to said one of said at least two members to aim said ultrasonic receiver at said operational field.

8. A combination as claimed in claim 7 wherein said mounting means comprises a bracket angularly supporting said ultrasonic transmitter on a first side of said one of said at least two members to aim said ultrasonic transmitter at said operational field and angularly supporting said ultrasonic receiver on a second side of said one of said at least two members opposite to said first side to aim said ultrasonic receiver at said operational field.

9. A combination as claimed in claim 1 wherein said ultrasonic means operates at a frequency of approximately 20 megahertz.

10. A combination of an ultrasonic sensing system and a surgical instrument having a distal end for performing a surgical step and a proximal end for activating performance of said surgical step, said combination comprising:

ultrasonic transducer means associated with said distal end of said surgical instrument for transmitting ultrasonic energy to an operational field defined by said distal end of said surgical instrument, for receiving ultrasonic energy reflected from said operational field, and for generating signals representative of ultrasonic energy received by said ultrasonic transducer means;

circuit means, coupled to said ultrasonic transducer means and responsive to said signals, for activating said transducer means to transmit said ultrasonic energy and for receiving and analyzing said signals from said ultrasonic transducer means; and alerting means coupled to said circuit means for informing a user of said surgical instrument of the contents of said operational field, said alerting means comprising tactile transducer means, coupled to said proximal end of said surgical instrument, for tactilely alerting said user.

11. A combination of an ultrasonic sensing system and a surgical instrument having a distal end for performing a surgical step and a proximal end for activating performance of said surgical step, said combination comprising:

ultrasonic transducer means associated with said distal end of said surgical instrument for transmitting ultrasonic energy to an operational field defined by said distal end of said surgical instrument, for receiving ultrasonic energy reflected from said operational field, and for generating signals representative of ultrasonic energy received by said ultrasonic transducer means;

circuit means, coupled to said ultrasonic transducer means and responsive to said signals, for activating said transducer means to transmit said ultrasonic energy and for receiving and analyzing said signals from said ultrasonic transducer means; and alerting means coupled to said circuit means for informing a user of said surgical instrument of the contents of said operational field, said surgical instrument comprising a surgical fastener applier with said distal end comprising a fastener ejection end and said proximal end comprising a handle grasped and operated by said user, said circuit means being housed within said handle and interconnected to said transducer means by wires extending from said handle to said fastener ejection end.

12. A combination of ultrasonic sensing system and a surgical instrument having a distal end for performing a surgical step and a proximal end for activating performance of said surgical step, said combination comprising:

ultrasonic transducer means associated with said distal end of said surgical instrument for transmitting ultrasonic energy to an operational field defined by said distal end of said surgical instrument, for receiving ultrasonic energy reflected from said operational field, and for generating signals representative of ultrasonic energy received by said ultrasonic transducer means;

circuit means, coupled to said ultrasonic transducer means and responsive to said signals, for activating said transducer means to transmit said ultrasonic energy and for receiving and analyzing said signals from said ultrasonic transducer means;

alerting means coupled to said circuit means for informing a user of said surgical instrument of the contents of said operational field; and power control means coupled to said circuit means and said surgical instrument for connecting power to said circuit means only while said surgical instrument is at least partially activated.

13. A combination of an endoscopic surgical instrument and an ultrasonic sensing system, said combination comprising:

a distal end of said endoscopic surgical instrument for performing a surgical procedure;

a proximal end of said endoscopic surgical instrument for activating performance of said surgical procedure;

ultrasonic transducer means associated with said distal end of said endoscopic surgical instrument for transmitting ultrasonic energy to an operational field defined by said distal end of said endoscopic surgical instrument, for receiving ultrasonic energy reflected from said operational field, and for generating signals representative of ultrasonic energy received by said ultrasonic transducer means from said operational field;

circuit means coupled to said ultrasonic transducer means for driving said transducer means to transmit said ultrasonic energy and for receiving and analyzing said signals from said ultrasonic transducer means, said circuit means being housed in said proximal end of said endoscopic surgical instrument and interconnected to said ultrasonic transducer means by wires extending from said proximal end to said distal end; and alerting means coupled to said circuit means for informing a user of said surgical instrument of the contents of said operational field.

14. A combination as claimed in claim 13 wherein said circuit means comprises comparator means for comparing a doppler signal derived from said signals to a threshold signal for analyzing said signals.

15. A combination as claimed in claim 14 wherein said circuit means further comprises threshold adjustment means for setting said threshold signal.

16. A combination of an ultrasonic sensing system and a surgical instrument having a distal end for performing a surgical step and a proximal end for activating performance of said surgical step, said combination comprising:

ultrasonic transducer means associated with said distal end of said surgical instrument for transmitting ultrasonic energy to an operational field defined by said distal end of said surgical instrument, for receiving ultrasonic energy reflected from said operational field, and for generating signals representative of ultrasonic energy received by said ultrasonic transducer means;

circuit means, coupled to said ultrasonic transducer means and responsive to said signals, for activating said transducer means to transmit said ultrasonic energy and for receiving and analyzing said signals from said ultrasonic transducer means; and alerting means coupled to said circuit means for informing a user of said surgical instrument of the contents of said operational field, said alerting means comprising tactile transducer means coupled to said proximal end of said surgical instrument for tactilely alerting said user.

17. A method of operating an endoscopic surgical instrument having a distal end for performing a surgical procedure within an operational field defined by movable members of said distal end and a proximal end for activating performance of said surgical procedure by said movable members within said operational field, said method comprising the steps of:

transmitting ultrasonic energy to said operational field of said surgical instrument;

receiving ultrasonic energy reflected from said operational field of said surgical instrument;

generating doppler signals representative of the contents of said operational field in response to reflected ultrasonic energy received from said operational field;

analyzing said doppler signals to determine the nature of the contents of said operational field of said surgical instrument;

informing the user of said surgical instrument of the contents of said operational field; and operating said surgical instrument to perform said surgical procedure by movement of said movable members in response to information confirming that the contents of said operational field are appropriate for said surgical procedure.

18. A method of operating an endoscopic surgical instrument as claimed in claim 17 wherein the step of analyzing said doppler signals comprises comparing said doppler signals to a threshold and the step of informing the user of said surgical instrument of the contents of said operational field comprises activating an alerting device while said signals exceed said threshold.

19. A method of operating an endoscopic surgical instrument as claim in claim 18 further comprises the step of adjusting said threshold.

20. A method of operating an endoscopic surgical instrument as claim in claim 18 wherein said step of informing the user of the contents of said operational field comprises the step of activating audible transducer means for audibly informing said user.

21. A method of operating a surgical instrument having a distal end for performing a surgical procedure within an operational field defined by said distal end and a proximal end for activating performance of said surgical procedure within said operational field, said method comprising the steps of:

transmitting ultrasonic energy to said operational field of said surgical instrument;

receiving ultrasonic energy reflected from said operational field of said surgical instrument;

generating doppler signals representative of the contents of said operational field in response to reflected ultrasonic energy received from said operational field;

analyzing said doppler signals to determine the nature of the contents of said operational field of said surgical instrument;

informing the user of said surgical instrument of the contents of said operational field by activating tactile transducer means accessible to said user for tactilely informing said user; and operating said surgical instrument to perform said surgical procedure in response to information confirming that the contents of said operational field are appropriate for said surgical procedure.

22. A method of operating a surgical instrument having a distal end for performing a surgical procedure within an operational field defined by said distal end and a proximal end for activating performance of said surgical procedure within said operational field, said method comprising the steps of:

transmitting ultrasonic energy to said operational field of said surgical instrument;

receiving ultrasonic energy reflected from said operational field of said surgical instrument;

generating doppler signals representative of the contents of said operational field in response to reflected ultrasonic energy received from said operational field;

analyzing said doppler signals to determine the nature of the contents of said operational field of said surgical instrument;

informing the user of said surgical instrument of the contents of said operational field;

operating said surgical instrument to perform said surgical procedure in response to information confirming that the contents of said operational field are appropriate for said surgical procedure; and enabling the performance of the foregoing steps only while said surgical instrument is at least partially operated.

23. A method of operating a surgical instrument having a distal end for performing a surgical procedure within an operational field defined by said distal end and a proximal end for activating performance of said surgical procedure within said operational field, said method comprising the steps of:

transmitting ultrasonic energy to said operational field of said surgical instrument;

receiving ultrasonic energy reflected from said operational field of said surgical instrument;

generating doppler signals representative of the contents of said operational field in response to reflected ultrasonic energy received from said operational field;

analyzing said doppler signals to determine the nature of the contents of said operational field of said surgical instrument;

informing the user of said surgical instrument of the contents of said operational field by activating tactile transducer means accessible to said user for tactilely informing said user; and operating said surgical instrument to perform said surgical procedure in response to information confirming that the contents of said operational field are appropriate for said surgical procedure.

* * * * *

UNITED STATES PATENT AND TRADEMARK OFFICE
CERTIFICATE OF CORRECTION

PATENT NO. :    5,275,166
DATED      :    January 4, 1994
INVENTOR(S) :   Jeffrey J. Vaitekunas & Thomas F. Charlebois It is certified that error appears in the above-indentified patent and that said Letters Patent is hereby corrected as shown below:

Title page, item [54] line 1, and col. 1, line 1,
In the title, "METHOD AND APPARATUS" should be
-- METHODS AND APPARATUS --.

Column 11, lines 28-29, "said digital end" should be --said distal end--.

Signed and Sealed this

Twenty-eighth Day of June, 1994

Attest:

BRUCE LEHMAN

*Attesting Officer*       *Commissioner of Patents and Trademarks*